United States Patent
Ko et al.

(10) Patent No.: US 9,408,589 B2
(45) Date of Patent: Aug. 9, 2016

(54) ULTRASONIC TRANSDUCER, ULTRASONIC PROBE, AND ULTRASOUND IMAGE DIAGNOSIS APPARATUS

(71) Applicant: SAMSUNG ELECTRONICS CO., LTD., Suwon-si, Gyeonggi-do (KR)

(72) Inventors: Hyun-phill Ko, Seongnam-si (KR); Jong-mock Lee, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 395 days.

(21) Appl. No.: 13/708,186

(22) Filed: Dec. 7, 2012

(65) Prior Publication Data

US 2013/0281857 A1    Oct. 24, 2013

(30) Foreign Application Priority Data

Apr. 23, 2012  (KR) .................. 10-2012-0042179

(51) Int. Cl.
| | |
|---|---|
| *A61B 8/00* | (2006.01) |
| *H01L 41/047* | (2006.01) |
| *A61B 8/14* | (2006.01) |
| *A61B 8/08* | (2006.01) |
| *H01L 41/25* | (2013.01) |
| *B06B 1/06* | (2006.01) |

(52) U.S. Cl.
CPC .............. *A61B 8/4494* (2013.01); *A61B 8/14* (2013.01); *A61B 8/4444* (2013.01); *A61B 8/5207* (2013.01); *B06B 1/0629* (2013.01); *H01L 41/0474* (2013.01); *H01L 41/25* (2013.01); *Y10T 29/42* (2015.01)

(58) Field of Classification Search
CPC ...... A61B 8/4494; A61B 8/14; A61B 8/4444; A61B 8/5207; H01L 41/0474; H01L 41/25
See application file for complete search history.

(56) References Cited

U.S. PATENT DOCUMENTS

| | | | |
|---|---|---|---|
| 448,075 A | 3/1891 | Rassweiler | |
| 4,962,332 A * | 10/1990 | Rokurohta et al. | 310/335 |
| 5,329,498 A * | 7/1994 | Greenstein | 367/155 |
| 5,704,105 A | 1/1998 | Venkataramani et al. | |
| 5,744,898 A | 4/1998 | Smith et al. | |

(Continued)

FOREIGN PATENT DOCUMENTS

| | | |
|---|---|---|
| CN | 1331842 | 1/2002 |
| CN | 1753201 | 3/2006 |

(Continued)

OTHER PUBLICATIONS

Korean Office Action for corresponding Korean Application 10-2012-0042179; dated Sep. 9, 2013.

(Continued)

*Primary Examiner* — Bo J Peng
(74) *Attorney, Agent, or Firm* — Staas & Halsey LLP

(57) ABSTRACT

An ultrasonic transducer, an ultrasonic probe, and an ultrasound image diagnosis apparatus include a plurality of piezoelectric elements arranged in at least one column; individual electrodes provided on at least one surface of top and bottom surfaces of each of the piezoelectric elements; side electrodes extending toward one side surfaces of the piezoelectric elements from the individual electrodes; and a side electrode substrate including wiring lines that are bonded to the one side surfaces of the piezoelectric elements and are electrically connected to the side electrodes, respectively.

23 Claims, 24 Drawing Sheets

(56) References Cited

U.S. PATENT DOCUMENTS

| | | | |
|---|---|---|---|
| 5,815,054 A * | 9/1998 | Vojak et al. | 333/191 |
| 6,043,590 A | 3/2000 | Gilmore | |
| 6,640,634 B2 | 11/2003 | Hashimoto et al. | |
| 6,798,059 B1 | 9/2004 | Ishihara et al. | |
| 7,053,530 B2 | 5/2006 | Baumgartner et al. | |
| 7,362,036 B2 | 4/2008 | Sasaki | |
| 8,872,412 B2 | 10/2014 | Tezuka et al. | |
| 2002/0060092 A1 | 5/2002 | Kumakura | |
| 2002/0073781 A1 * | 6/2002 | Hashimoto et al. | 73/641 |
| 2008/0015443 A1 | 1/2008 | Hosono et al. | |
| 2010/0204583 A1 | 8/2010 | Rhim et al. | |
| 2010/0241003 A1 | 9/2010 | Jung | |
| 2010/0241004 A1 | 9/2010 | Jung et al. | |
| 2010/0324425 A1 | 12/2010 | Kim et al. | |
| 2011/0248603 A1 * | 10/2011 | Tezuka et al. | 310/314 |
| 2011/0295124 A1 | 12/2011 | Shikata et al. | |

FOREIGN PATENT DOCUMENTS

| | | |
|---|---|---|
| CN | 102218394 | 10/2011 |
| JP | 59-91800 | 5/1984 |
| JP | 7-177599 | 7/1995 |
| JP | 2008-022266 | 1/2008 |
| JP | 2009-177302 | 8/2009 |
| JP | 2012-19326 | 1/2012 |
| KR | 10-2009-0008498 | 1/2009 |
| KR | 10-2010-0091466 | 8/2010 |
| KR | 10-2010-0104534 | 9/2010 |
| KR | 10-2010-0104535 | 9/2010 |
| KR | 10-2010-0137842 | 12/2010 |

OTHER PUBLICATIONS

PCT International Search Report mailed Apr. 26, 2013 in corresponding International Application No. PCT/KR2012/011554.

Korean Office Action issued Jun. 11, 2013 in corresponding Korean Application No. 10-2012-0042179.

Extended European Search Report issued Mar. 17, 2016 in corresponding European Patent Application No. 12875069.2.

* cited by examiner

ULTRASONIC TRANSDUCER, ULTRASONIC PROBE, AND ULTRASOUND IMAGE DIAGNOSIS APPARATUS

CROSS-REFERENCE TO RELATED APPLICATIONS

This application claims the benefit of Korean Patent Application No. 10-2012-0042179, filed on Apr. 23, 2012, in the Korean Intellectual Property Office, the disclosure of which is incorporated herein in its entirety by reference.

BACKGROUND

1. Field

One or more embodiments relate to an ultrasonic transducer, an ultrasonic probe, and an ultrasound image diagnosis apparatus, and more particularly, to an ultrasonic transducer having an improved electrode connection structure, an ultrasonic probe, and an ultrasound image diagnosis apparatus.

2. Description of the Related Art

An ultrasound image diagnosis apparatus is an apparatus that radiates an ultrasonic wave signal to a desired inner site of a body via a body surface of a subject and uses information about a reflected ultrasonic wave signal (ultrasonic wave echo signal) to obtain an image about a fault of soft tissues or blood flow in a noninvasive manner. Compared to other image diagnosis apparatuses, such as an X-ray diagnosis apparatus, a computerized tomography (CT) scanner, a magnetic resonance image (MRI) apparatus, or a nuclear medicine diagnosis apparatus, the ultrasound image diagnosis apparatus is small and inexpensive, displays an image in real time, and has high stability due to no radiation of, for example, X-rays. Due to these advantages, the ultrasound image diagnosis apparatus is widely used for heart, abdomen, urinary system, and obstetrics diagnoses.

The ultrasound image diagnosis apparatus may include, for example, an ultrasonic probe that transmits an ultrasonic wave signal to a subject and receives an ultrasonic wave echo signal reflected from the subject to obtain an ultrasonic image of the subject. The ultrasonic probe may include, for example a transducer, a case having an open top end, and a cover that is coupled to the top end of the case and directly contacts a surface of a subject. In this regard, the transducer may include, for example, a piezoelectric layer that includes a piezoelectric material for reversibly converting an electric signal and an acoustic signal during vibration, an acoustic matching layer that may reduce an acoustic impedance difference between the piezoelectric layer and the subject so as to allow an ultrasonic wave produced by the piezoelectric layer to be transmitted to the subject as much as possible, an acoustic lens layer that may allow an ultrasonic wave progressing forward from the piezoelectric layer to be focused on a particular point, and a sound wave absorption layer that may prevent an ultrasonic wave from progressing backward from the piezoelectric layer to prevent image distortion. In the piezoelectric layer of the transducer, a plurality of piezoelectric elements to which electrical signals are independently applied may be arranged. Electrical wiring lines with respect to the piezoelectric elements may be factors in determining the characteristics, shape, manufacturing process, and costs of the transducer.

SUMMARY

Additional aspects and/or advantages will be set forth in part in the description which follows and, in part, will be apparent from the description, or may be learned by practice of the invention.

One or more embodiments may provide an ultrasonic transducer having an improved electrode connection structure for electrical connection of a piezoelectric layer, an ultrasonic probe, and an ultrasound image diagnosis apparatus.

According to an aspect of one or more embodiments, there may be provided an ultrasonic transducer which may include: a plurality of piezoelectric elements arranged in at least one column; individual electrodes provided on at least one surface of top and bottom surfaces of each of the piezoelectric elements; side electrodes extending toward one side surfaces of the piezoelectric elements from the individual electrodes; and/or a side electrode substrate including wiring lines that are bonded to the one side surfaces of the piezoelectric elements and are electrically connected to the side electrodes, respectively.

The side electrodes of the piezoelectric elements located in one column may have different heights.

The heights of the side electrodes of the piezoelectric elements located in one column may be gradually decreased or increased in a lengthwise direction of the column.

The wiring lines of the side electrode substrate may include, for example, first parts respectively facing the side electrodes, second parts extending toward one side ends of the side electrode substrate, and third parts exposed by the one side ends of the side electrode substrate.

A substrate body of the side electrode substrate may be formed of an anisotropic electroconductive material having an electroconductive property in a thickness direction and having an insulating property in a surface direction, and the wiring lines of the side electrode substrate may be provided in a surface opposite to the surface where the substrate meets the side electrodes of the piezoelectric elements.

The substrate body of the side electrode substrate may be formed of an electric insulating material, and the wiring lines of the side electrode substrate may be provided in the surface where the substrate meets the side electrodes.

The piezoelectric elements may be arranged in a two-dimensional array to be spaced apart from one another in columns and lines, and a plurality of the side electrode substrates may be inserted into gaps between the columns of the piezoelectric elements.

Heights of the side electrodes of the piezoelectric elements of a first column may be gradually decreased in a lengthwise direction of the column, and heights of side electrodes of the piezoelectric elements of a second column adjacent to the first column may be gradually increased in the lengthwise direction of the column.

The wiring lines of the side electrode substrates may include, for example, first parts respectively facing the side electrodes, second parts extending toward side ends of the side electrode substrates, and third parts exposed by the side ends of the side electrode substrates, and the side ends by which the third parts are exposed of a first side electrode substrate bonded to the piezoelectric elements of the first column may be opposite to the side ends by which the third parts are exposed of a second side electrode substrate bonded to the piezoelectric elements of the second column.

The ultrasonic transducer may further include a first connection substrate electrically connected to the exposed third parts of the first side electrode substrate and a second connection substrate electrically connected to the exposed third parts of the second side electrode substrate.

Heights of the side electrodes of the piezoelectric elements of all columns may be gradually decreased or increased in the same direction.

The wiring lines of the side electrode substrates may include, for example, first parts respectively facing the side electrodes, second parts extending toward one side ends of the side electrode substrate, and third parts exposed by the one side ends of the side electrode substrate, wherein the side ends by which the third parts may be exposed of the side electrode substrates may be arranged in the same direction.

The ultrasonic transducer may further include one connection substrate electrically connected to the exposed third parts of the side electrode substrates.

A substrate body of the side electrode substrate may be formed of a sound absorbing material.

A substrate body of the side electrode substrate may be formed of a flexible material.

The individual electrodes may be signal electrodes respectively provided under the piezoelectric elements, and common electrodes may be respectively provided on the piezoelectric elements.

The common electrodes further may include upper electrodes respectively provided on top surfaces of the piezoelectric elements and an upper electrode plate that may be provided on top surfaces of the upper electrodes and that is commonly and electrically connected to the upper electrodes.

The ultrasonic transducer may further include an acoustic matching layer provided between the upper electrodes and an upper electrode layer, and the acoustic matching layer may be formed of a conductive material, or at least a part of an outer surface of the acoustic matching layer is coated with a conductive material.

The individual electrodes may be signal electrodes respectively provided on the piezoelectric elements, and a common electrode may be provided under the piezoelectric elements.

The ultrasonic transducer may further include a rear surface supporting unit provided under the piezoelectric elements to support the piezoelectric elements, wherein the rear surface supporting unit may be formed of a conductive material and may be electrically connected to the common electrode.

A plurality of kerfs may be formed in portions of the rear surface supporting unit contacting the piezoelectric elements to correspond to gaps between the piezoelectric elements.

At least a portion of the rear surface supporting unit contacting the piezoelectric elements may be formed of a sound absorbing material.

According to another aspect of one or more embodiments, there may be provided an ultrasonic probe which may include, for example: an ultrasonic transducer; and a housing accommodating the ultrasonic transducer, wherein the ultrasonic transducer may include, for example: a plurality of piezoelectric elements arranged in at least one column; individual electrodes provided on at least one surface of top and bottom surfaces of each of the piezoelectric elements; side electrodes extending toward one side surfaces of the piezoelectric elements from the individual electrodes; and/or a side electrode substrate including wiring lines that are bonded to the one side surfaces of the piezoelectric elements and are electrically connected to the side electrodes, respectively.

According to another aspect of one or more embodiments, there is provided an ultrasound image diagnosis apparatus which may include, for example: an ultrasonic probe including an ultrasonic transducer and a housing accommodating the ultrasonic transducer; and a signal processor for generating an ultrasonic wave image based on an ultrasonic wave echo signal detected by the ultrasonic probe, wherein the ultrasonic transducer may include, for example: a plurality of piezoelectric elements arranged in at least one column; individual electrodes provided on at least one surface of top and bottom surfaces of each of the piezoelectric elements; side electrodes extending toward one side surfaces of the piezoelectric elements from the individual electrodes; and a side electrode substrate which may include wiring lines that may be bonded to the one side surfaces of the piezoelectric elements and may be electrically connected to the side electrodes, respectively.

According to another aspect of one or more embodiments, there is provided a method of manufacturing an ultrasonic transducer, the method may include, for example: providing a piezoelectric layer; forming an electrode layer on at least one surface of the piezoelectric layer; forming one block by bonding a support structure to a bottom surface of the piezoelectric layer; providing a plurality of sub-blocks by cutting a block including the support structure and the piezoelectric layer in a vertical direction at equal intervals; forming a side electrode electrically connected to an electrode layer of the piezoelectric layer in one side surface of the block including the support structure and the piezoelectric layer; forming a plurality of kerfs at equal intervals from uppermost portions of the sub-blocks to a predetermined position of the support structure; providing a side electrode substrate having wiring patterns corresponding to side electrodes of the sub-blocks; bonding the side electrode substrate to the sub-blocks in which the kerfs are formed; bonding the sub-blocks to which the side electrode substrate is bonded to a supporting block in a width direction; and/or bonding a connection substrate to a side surface of the supporting block to which the sub-blocks are bonded.

The method may further include an operation of detecting and selecting a piezoelectric property for each sub-block to which the side electrode substrate is bonded before the sub-blocks to which the side electrode substrate is bonded are bonded to the supporting block in the width direction.

The ultrasonic transducer, the ultrasonic probe, and the ultrasound image diagnosis apparatus according to the above-described embodiments of the present invention may have the following effects.

Firstly, electrical signals may be respectively applied to a plurality of piezoelectric elements via a side electrode, and thus an electric connecting structure via the side electrode may be easily applied to a two-dimensional arrayed ultrasonic transducer, and further to a stacked structured ultrasonic transducer.

Secondly, when a single ultrasonic transducer is manufactured, a plurality of piezoelectric elements may be assembled in units of columns, and thus the piezoelectric elements may be tested in units of columns to decrease dispersion of piezoelectric characteristics, thereby possibly reducing a fluctuation in performance of the ultrasonic transducer.

BRIEF DESCRIPTION OF THE DRAWINGS

The above and other features and advantages of one or more embodiments will become more apparent by describing in detail exemplary embodiments with reference to the attached drawings in which.

DETAILED DESCRIPTION

Figure 1:
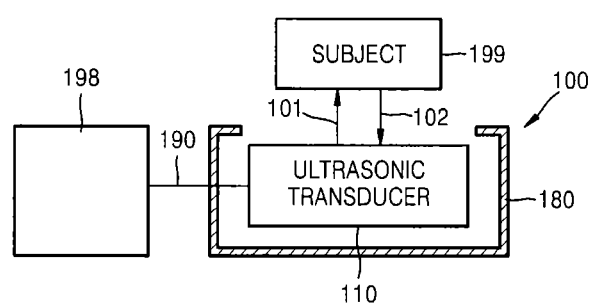
FIG. 1 is a block diagram illustrating an ultrasound image diagnosis apparatus according to one or more embodiments.

Reference will now be made in detail to one or more embodiments, illustrated in the accompanying drawings, wherein like reference numerals refer to like elements throughout. In this regard, embodiments of the present invention may be embodied in many different forms and should not be construed as being limited to embodiments set forth herein, as various changes, modifications, and equivalents of the systems, apparatuses and/or methods described herein will be understood to be included in the invention by those of ordinary skill in the art after embodiments discussed herein are understood. Accordingly, embodiments are merely described below, by referring to the figures, to explain aspects of the present invention. In the drawings, the thicknesses of layers and regions are exaggerated for clarity. Expressions such as "at least one of," when preceding a list of elements, modify the entire list of elements and do not modify the individual elements of the list.

FIG. 1 is a block diagram illustrating an ultrasound image diagnosis apparatus according to one or more embodiments.

Referring to FIG. 1, the ultrasound image diagnosis apparatus of the current embodiment may include an ultrasonic probe 100 and a signal processor 198. The ultrasonic probe 100 may include an ultrasonic transducer 110 that may transmit an ultrasonic wave 101 to a subject 199, for example, a human body, and may receive an ultrasonic wave 102 reflected from the subject 199, and a housing 180 for accommodating the ultrasonic transducer 110. The ultrasonic probe 100 may be electrically connected to the signal processor 198 via a cable 190. The signal processor 198 may control the ultrasonic probe 100 and may generate an image of the subject 199 based on an echo signal detected by the ultrasonic probe 100.

Figure 2:
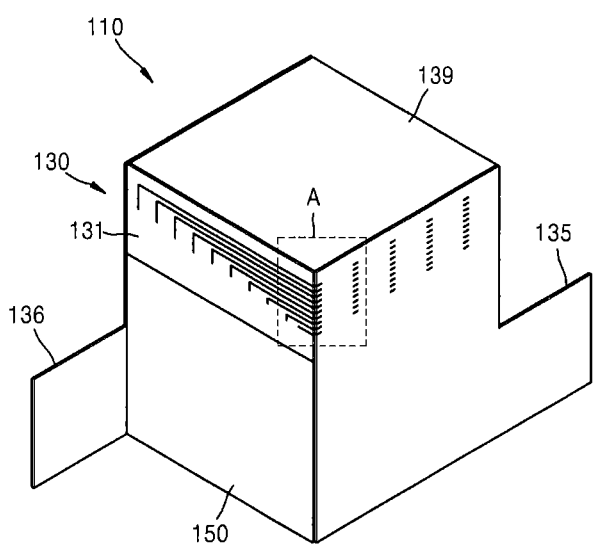
FIG. 2 is a perspective view of an ultrasonic transducer according to one or more embodiments.
Figure 3:
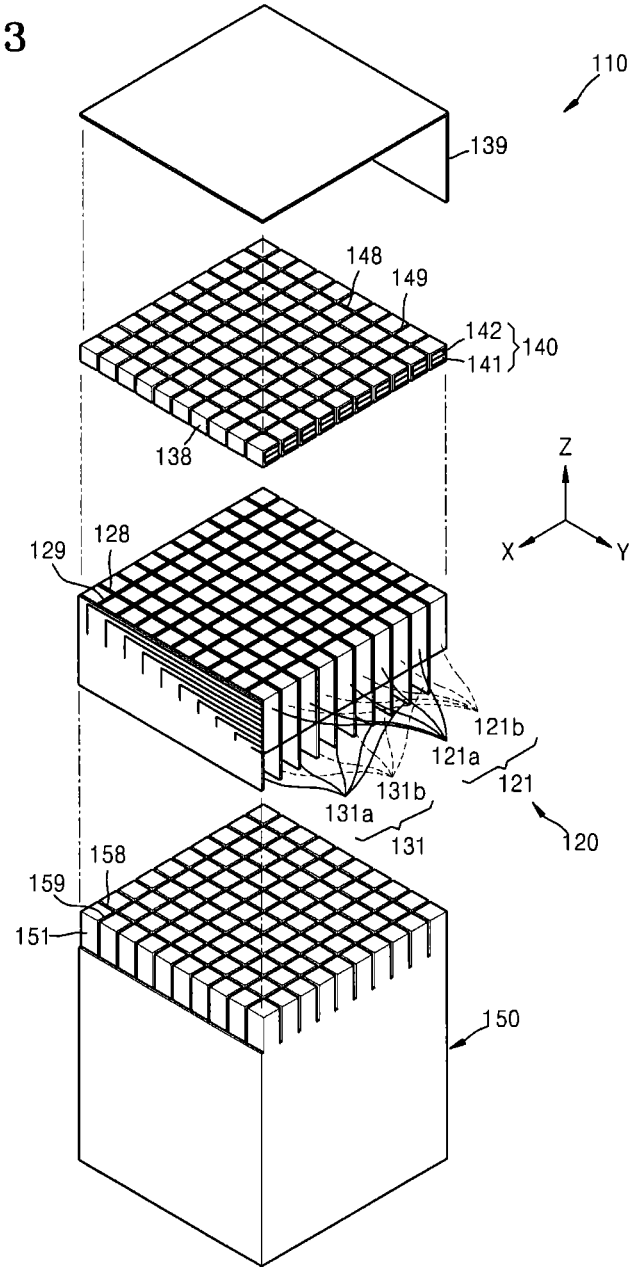
FIG. 3 is an exploded perspective view of an ultrasonic transducer according to one or more embodiments.

FIG. 2 is a perspective view of the ultrasonic transducer 110 accommodated in the ultrasonic probe 100 according to one or more embodiments. FIG. 3 is an exploded perspective view of the ultrasonic transducer 110 according to one or more embodiments. For convenience of description, first and second connection substrates 135 and 136 are omitted in FIG. 3. Also, in FIG. 3, although it is shown as if upper ends of a plurality of side electrode substrates 131 correspond with top surfaces of piezoelectric elements 121, the upper ends of the side electrode substrates 131 may extend to correspond with top surfaces of a plurality of acoustic matching layers 140.

Referring to FIGS. 2 and 3, the ultrasonic transducer 110 according to one or more embodiments may include a piezoelectric layer 120, an electrode connecting unit 130 for electrical connection of the piezoelectric layer 120, acoustic matching layers 140 disposed on the piezoelectric layer 120, and a rear surface supporting unit 150 disposed under the piezoelectric layer 120.

The piezoelectric layer 120 may include a plurality of piezoelectric elements 121. The piezoelectric elements 121 may be individually operated and may be arranged spaced apart from one another on a two-dimensional plane in m lines and n columns to possibly avoid reciprocal interference. In this regard, m and n are natural numbers and may be the same or different. The piezoelectric elements 121 may include a plurality of piezoelectric elements 121a of odd numbered columns and a plurality of piezoelectric elements 121b of even numbered columns. Patterns of side electrodes of the piezoelectric elements 121a of the odd numbered columns may be different from patterns of side electrodes of the piezoelectric element 121b of the even numbered columns, which will be described later.

The electrode connecting unit 130 may include a plurality of side electrode substrates 131 electrically connected to lower electrodes 124 (see FIG. 4) of the piezoelectric elements 121, first and second connection substrates 135 and 136 electrically connected to the side electrode substrates 131, and a common electrode plate 139 electrically connected to upper electrodes 123 (see FIG. 4) of the piezoelectric elements 121 via the top surfaces of the acoustic matching layers 140.

The side electrode substrates 131 may be attached to side surfaces of the piezoelectric elements 121. As described above, as the piezoelectric elements 121 may be arranged spaced apart from one another in lines and columns, horizontal gaps 128 and vertical gaps 129 may be formed between the piezoelectric elements 121. Accordingly, a first side electrode substrate 131 may be attached to outer surfaces of a first column of the piezoelectric elements 121, and the rest of side electrode substrates 131 may be inserted into the horizontal gaps 128 of the piezoelectric elements 121. The number of side electrode substrates 131 may be the same as the number of columns of the piezoelectric elements 121. The side electrode substrates 131 may be formed of a sound absorbing material so as to suppress interference due to adjacent piezoelectric elements 121 when the piezoelectric elements 121 send and receive an ultrasonic wave. From among the gaps between the piezoelectric elements 121, a sound absorbing material may be filled in the vertical gaps 129 into which the side electrode substrates 131 are not inserted, thereby suppressing interference due to adjacent piezoelectric elements 121.

The patterns of the side electrodes of the piezoelectric elements 121a of the odd numbered columns may be different from the patterns of the side electrodes of the piezoelectric element 121b of the even numbered columns. Correspondingly, wiring patterns of first side electrode substrates 131a of the odd numbered columns may be different from wiring patterns of second side electrode substrates 131b of the even numbered columns, which will be described later.

The first and second connection substrates 135 and 136 may be substrates for integrating wiring lines of the side electrode substrates 131. The first and second connection substrates 135 and 136 may be attached to outer surfaces of the piezoelectric elements 121. The first and second connection substrates 135 and 136 may be flexible printed circuit boards or hard printed circuit boards. At least one of the first and second connection substrates 135 and 136 may further include a circuit for processing electric signals input to the piezoelectric elements 121 and electric signals output from the piezoelectric elements 121. The wiring lines integrated by the first and second connection substrates 135 and 136 may be electrically connected to the signal processor 198 via the cable 190 (see FIG. 1).

The acoustic matching layers 140 may be provided on the piezoelectric layer 120. The acoustic matching layers 140 may be respectively provided on the piezoelectric elements 121 to be arranged spaced apart from one another. In other words, horizontal gaps 148 and vertical gaps 149 corresponding to the horizontal gaps 128 and vertical gaps 129 between the piezoelectric elements 121 may be extended to the acoustic matching layers 140. The acoustic matching layers 140 properly match acoustic impedance of the piezoelectric layer 120 and acoustic impedance of the subject 199 (see FIG. 1) to possibly reduce a loss of an ultrasonic wave transmitted to the subject 199 or an ultrasonic wave transmitted from the subject 199. The acoustic matching layers 140 may promote matching of acoustic impedance between the subject 199 and the piezoelectric layer 120 by, for example, adjusting a physical parameter such as a thickness or acoustic impedance. For example, the acoustic matching layers 140 may include two layers 141 and 142 having different acoustic impedances. In other cases, the acoustic matching layers 140 may consist of a single layer or three or more layers. An acoustic lens (not shown) for focusing an ultrasonic wave traveling forward on a specific point may further be provided on the acoustic matching layers 140.

An intermediate electrode layer 138 for electrically connecting the upper electrodes 123 of the piezoelectric elements 121 and the common electrode plate 139 may be formed on outer surfaces of the acoustic matching layers 140. The acoustic matching layers 140 may be formed of a conductive material, and in this case, the intermediate electrode layer 138 may be omitted. Furthermore, when the acoustic matching layers 140 are formed of a conductive material, the upper electrodes 123 respectively provided on the piezoelectric elements 121 may also be omitted.

In one or more embodiments, the acoustic matching layers 140 may be respectively provided on the piezoelectric elements 121 to be arranged spaced apart from one another. However, the present invention is not limited thereto. For example, the acoustic matching layers 140 may be formed as an integrated single layer to be attached to the top surfaces of the piezoelectric elements 121.

The rear surface supporting unit 150 is a block for supporting the piezoelectric layer 120. An upper portion 151 of the rear surface supporting unit 150 may consist of unit blocks that are spaced apart from one another to correspond to the piezoelectric elements 121. In other words, grooves may be formed in the upper portion 151 of the rear surface supporting unit 150 to form horizontal gaps 158 and vertical gaps 159 respectively extending from the vertical gaps 128 and the horizontal gaps 129 between the piezoelectric elements 121. The rear surface supporting unit 150 may be entirely formed of an insulating material, or at least the upper portion 151 of the rear surface supporting unit 150 may be formed of an insulating material. Also, the upper portion 151 of the rear surface supporting unit 150 may be formed as a rear sound wave absorption layer so as to possibly properly control reflection of an ultrasonic wave generated from the piezoelectric layer 120, thereby possibly preventing image distortion by preventing a ultrasonic wave from traveling rearward of the piezoelectric layer 120.

Figure 4:
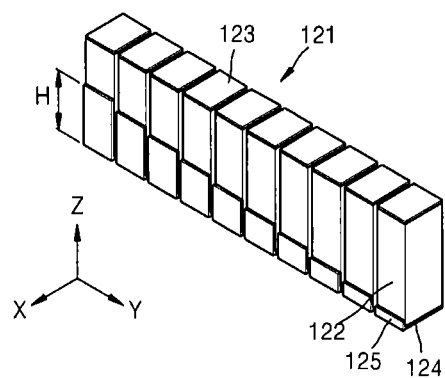
FIG. 4 is a view illustrating piezoelectric elements of an ultrasonic transducer according to one or more embodiments.

FIG. 4 is a view illustrating the piezoelectric elements 121 arranged in any one column from among the piezoelectric elements 121 arranged in lines and columns in the ultrasonic transducer 110 according to one or more embodiments. Referring to FIG. 4, each of the piezoelectric elements 121 may include a piezoelectric body 122 and the upper and lower electrodes 123 and 124 respectively provided on top and bottom surfaces of the piezoelectric body 122. The piezoelectric bodies 122 may be formed of a piezoelectric material in which an electrical signal may be converted to a sound signal and vice versa. For example, the piezoelectric bodies 122 may be formed of a lead zirconate titanate (PZT) ceramic, a PZNT single crystal including a solid solution of zinc lead niobate and lead titanate, a PZMT single crystal including a solid solution of magnesium lead niobate and lead titanate, or the like. The piezoelectric bodies 122 may be formed to have a pillar shape having at least one side surface. For example, the piezoelectric bodies 122 may be formed to have a rectangular parallelepiped shape. The shape of the piezoelectric bodies 122 may vary according to various designs. The upper electrodes 123 may be provided on the top surfaces of the piezoelectric bodies 122. The upper electrodes 123 may be a common electrode (or a ground electrode) of the piezoelectric elements 121. The upper electrodes 123 of the piezoelectric elements 121 may be electrically connected to the common electrode plate 139 via an intermediate electrode layer 138 which may be provided on the outer surfaces of the acoustic matching layers 140.

Figure 7:
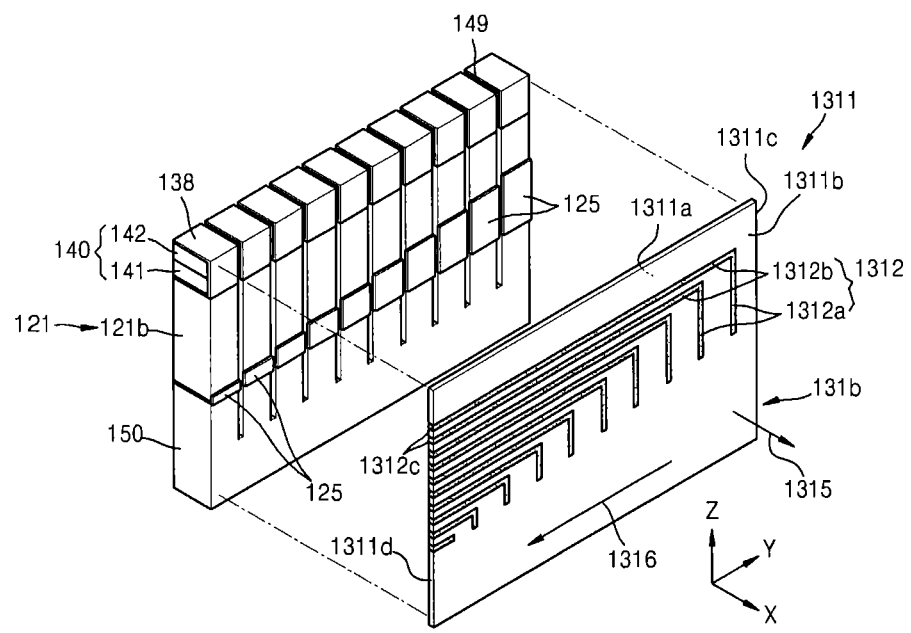
FIG. 7 is a view illustrating a second side electrode substrate attached to piezoelectric elements arranged in even numbered columns in an ultrasonic transducer according to one or more embodiments.

The lower electrodes 124 may be provided on the bottom surfaces of the piezoelectric bodies 122. The lower electrodes 124 may be individual electrodes provided in the piezoelectric elements 121 and may be signal electrodes to which individual signals are applied. The lower electrodes 124 may extend to one side surfaces of the piezoelectric bodies 122 to form side electrodes 125. The side electrodes 125 may be disposed on the side surfaces of the piezoelectric elements 121 arranged in a line in the same direction. Heights H of the side electrodes 125 may be formed to be different from one another. As shown in FIG. 4, the heights H of the side electrodes 125 may be formed to be gradually decreased in a column-wise direction (Y direction). As shown in FIG. 7, the heights H of the side electrodes 125 may be formed to be gradually increased in the column-wise direction (Y direction). In other cases, the heights H of the side electrodes 125 may be formed to be equal to one another.

Figure 5:
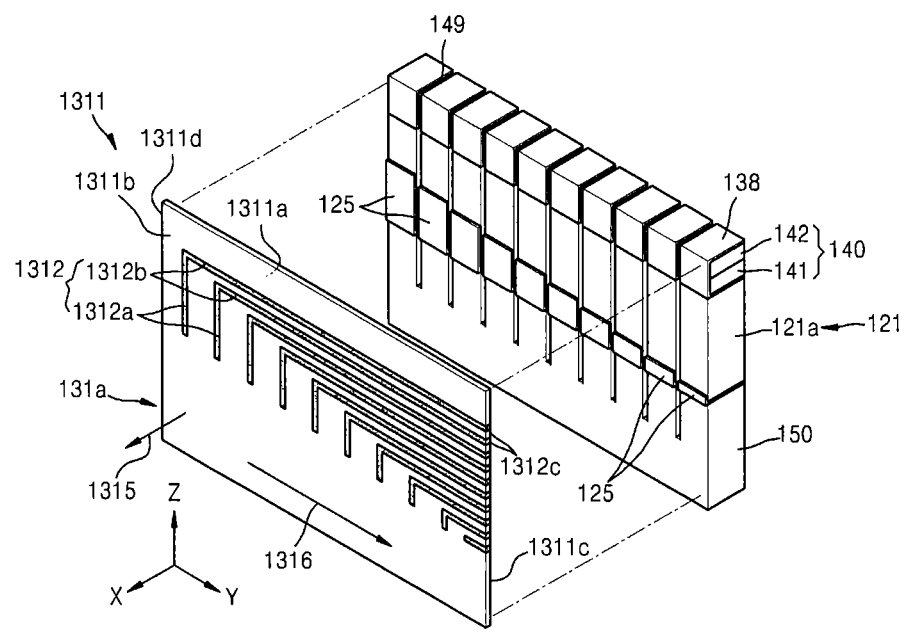
FIG. 5 is a view illustrating a first side electrode substrate attached to side surfaces of piezoelectric elements of odd numbered columns in an ultrasonic transducer according to one or more embodiments.

FIG. 5 is a view illustrating the first side electrode substrates 131a attached to side surfaces of piezoelectric elements 121a of the odd numbered columns from among the piezoelectric elements 121.

Referring to FIG. 5, the piezoelectric elements 121a of the odd numbered columns may include the side electrodes 125 formed to be decreased in height in the column-wise direction (Y direction).

Each of the first side electrode substrates 131a may include a substrate body 1311 and a plurality of wiring lines 1312. The substrate body 1311 of the current embodiment may be formed of an anisotropic electroconductive material. In other words, the substrate body 1311 may have an electroconductive property in a thickness direction 1315 but may have an insulating property in a surface direction 1316. A conductive rubber sheet, an insulating resin sheet containing electroconductive particles, and the like that may be used for the substrate body 1311 having an anisotropic electroconductive property are well known. In addition, the substrate body 1311 may be formed of a sound absorbing material to suppress interference between adjacent piezoelectric elements 121. A top end of the substrate body 1311 may correspond with top ends of the acoustic matching layers 140. A bottom end of the substrate body 1311 may cover at least a part of the rear surface supporting unit 150. First and second side ends 1311c and 1311d of the substrate body 1311 correspond with two side ends of the piezoelectric elements 121a of the odd numbered columns in the column-wise direction.

One surface 1311a of the substrate body 1311 may contact the side surfaces of the piezoelectric elements 121a of the odd numbered columns on which the side electrodes 125 may be provided. The wiring lines 1312 corresponding to the side electrodes 125 may be provided on another surface 1311b of the substrate body 1311. The wiring lines 1312 may include first parts 1312a that may at least partially overlap with positions of the side electrodes 125, second parts 1312b that may extend toward the first side end 1311c of the substrate body 1311, and third parts 1312c that may be exposed at the first side end 1311c of the substrate body 1311. The first parts 1312a of the wiring lines 1312 may at least partially overlap with the side electrodes 125 by interposing the substrate body 1311 therebetween. The substrate body 1311 may have an electroconductive property in the thickness direction 1315, and thus the side electrodes 125 and the first parts 1312a may be electrically connected to each other. The substrate body 1311 may have an insulating property in the surface direction 1316, and thus an electric insulating property may be maintained between adjacent wiring lines 1312. The second parts 1312b of the wiring lines 1312 may be arranged in parallel in a vertical direction (that is, a Z direction), and thus the heights H of the side electrodes 125 may be designed to be gradually decreased in the column-wise direction (Y direction) as described above, thereby possibly securing a space where the second parts 1312b of the wiring lines 1312 may be disposed.

Figure 6:
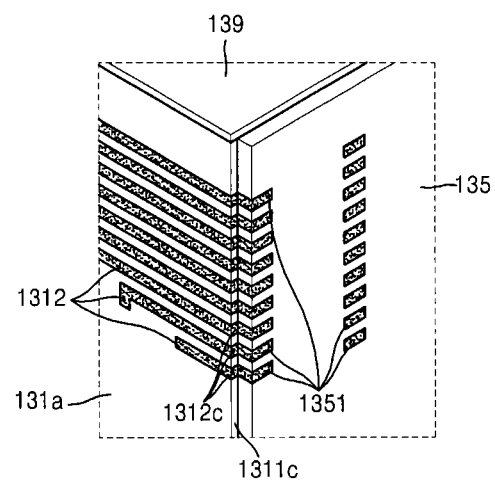
FIG. 6 is a view illustrating a side electrode substrate and a connection substrate bonded together in an ultrasonic transducer according to one or more embodiments.

FIG. 6 is an enlarged view of a part A of FIG. 2 in which the first side electrode substrates 131a and the first connection substrate 135 may be bonded together. Referring to FIG. 6, the first connection substrate 135 may be directly attached to the first side end 1311c of the first side electrode substrates 131a. A plurality of connection terminals 1351 may be provided in the first connection substrate 135 to face the first side end 1311c of the first side electrode substrates 131a of the odd numbered columns. Accordingly, the third parts 1312c of the wiring lines 1312 exposed by the first side end 1311c of the first side electrode substrates 131a may directly contact the connection terminals 1351 of the first connection substrate 135 to be electrically connected to each other.

FIG. 7 is a view illustrating the second side electrode substrates 131b attached to side surfaces of the piezoelectric elements 121b of the even numbered columns from among the piezoelectric elements 121. Referring to FIG. 7, the piezoelectric elements 121b of the even numbered columns may be substantially the same as the above-described piezoelectric elements 121a of the odd numbered columns except that heights of the side electrodes 125 may be formed to be gradually increased in the column-wise direction (Y direction).

Meanwhile, the second side electrode substrates 131b may be substantially the same as the first side electrode substrates 131a except for the patterns of the wiring lines 1312. The wiring lines 1312 of the second side electrode substrates 131b may include the first parts 1312a, which may at least partially overlap with positions of the side electrodes 125 of the piezoelectric elements 121b of the even numbered columns, the second parts 1312b may extend toward the second side end 1311d of the substrate body 1311, and the third parts 1312c may be exposed by the second side end 1311d of the substrate body 1311. In this regard, the second side end 1311d of the substrate body 1311 may be opposite to the first side end 1311c in the column-wise direction (Y direction).

Figure 8:
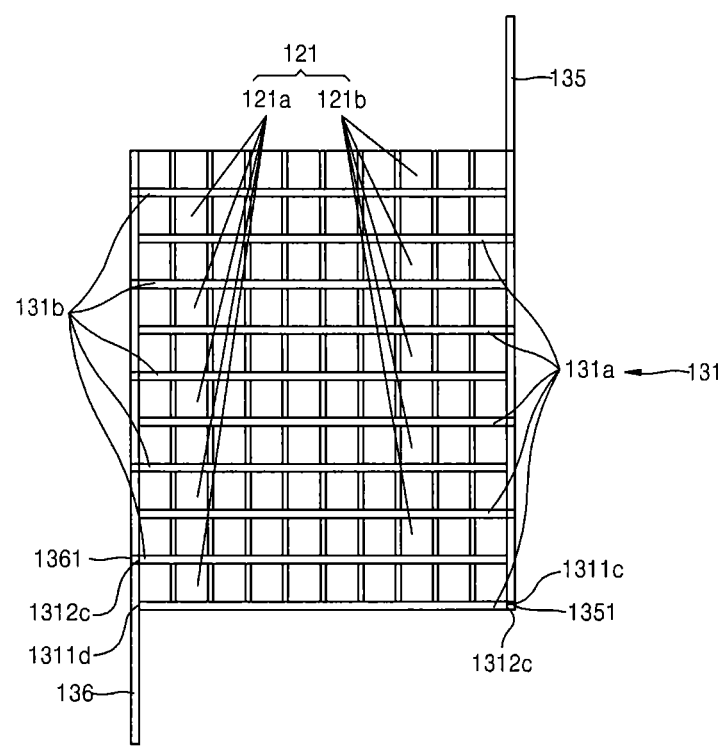
FIG. 8 is a view illustrating two connection substrates bonded to a side electrode substrate in an ultrasonic transducer according to one or more embodiments.

FIG. 8 is a view illustrating electrical connection between the first and second side electrode substrates 131a and 131b and the first and second connection substrates 135 and 136. Referring to FIG. 8, the side electrode substrates 131 may include the first side electrode substrates 131a and the second side electrode substrates 131b. The first side electrode substrates 131a may be attached to the side surfaces of the piezoelectric elements 121a of the odd numbered columns, and the second side electrode substrates 131b may be attached to the side surfaces of the piezoelectric element 121b of the even numbered columns. The wiring lines 1312 of the first side electrode substrates 131a may extend toward the first side end 1311c as shown in FIG. 5, and thus the third parts 1312c may be exposed by the first side end 1311c of the substrate body 1311 as shown in FIG. 5. The wiring lines 1312 of the second side electrode substrates 131b may extend toward the second side end 1311d as shown in FIG. 7, and thus the third parts 1312c may be exposed by the second side end 1311d. The first connection substrate 135 may be attached to the first side end 1311c of the first side electrode substrates 131a, and the connection terminals 1351 of the first connection substrate 135 may be electrically connected to the third parts 1312c of the wiring lines 1312 exposed by the first side end 1311c of the first side electrode substrates 131a. Similarly, the second connection substrate 136 may be attached to the second side end 1311d of the second side electrode substrates 131b, and a plurality of connection terminals 1361 of the second connection substrate 136 may be electrically connected to the third parts 1312c of the wiring lines 1312 exposed by the second side end 1311d of the second side electrode substrates 131b. As such, the first and second side electrode substrates 131a and 131b may be alternately and electrically connected to the first and second connection substrates 135 and 136, respectively, and sufficient intervals between the connection terminals 1351 of the first connection substrate 135 may be secured and also sufficient intervals between the connection terminals 1361 of the second connection substrate 136 may be secured, and thus tolerance may be secured in attaching the first and second connection substrates 135 and 136 to side ends of the first and second side electrode substrates 131a and 131b, respectively.

In one or more embodiments, all the first side electrode substrates 131a may be electrically connected to the first connection substrate 135, and all the second side electrode substrates 131b may be electrically connected to the second connection substrate 136, but the present invention is not limited thereto. For example, in FIG. 5, some of the wiring lines 1312 of the first side electrode substrates 131a may extend toward the first side end 1311c and the rest of the wiring lines 1312 may extend toward the second side end 1311d. In this case, some of the wiring lines 1312 of the first side electrode substrates 131a may be electrically connected to the first connection substrate 135, and the rest of the wiring lines 1312 of the first side electrode substrates 131a may be electrically connected to the second connection substrate 136. Similarly, in FIG. 7, some of the wiring lines 1312 of the second side electrode substrates 131b may extend toward the first side ends 1311c, and the rest of the wiring lines 1312 may extend toward the second side ends 1311d. In this case, some of the wiring lines 1312 of the second side electrode substrates 131b may be electrically connected to the first connection substrate 135, and the rest of the wiring lines 1312 of the second side electrode substrates 131b may be electrically connected to the second connection substrate 136.

Figure 9:
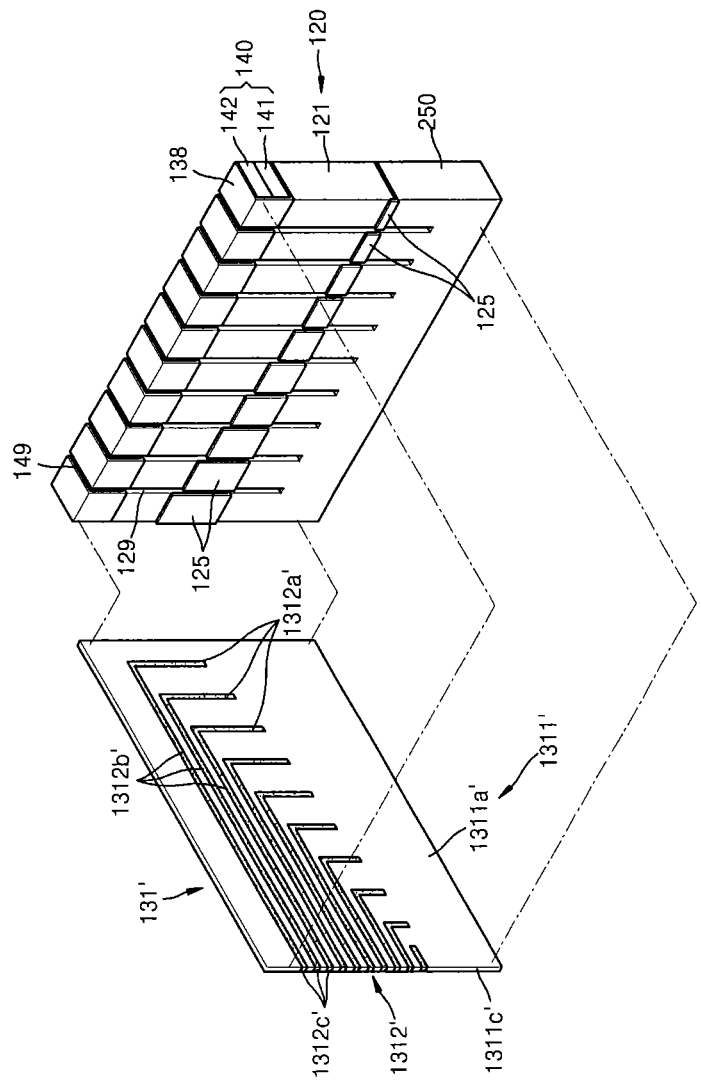
FIG. 9 is a view illustrating a side electrode substrate attached to side surfaces of piezoelectric elements in an ultrasonic transducer according to one or more embodiments.

FIG. 9 is a view illustrating a side electrode substrate attached to side surfaces of piezoelectric elements in an ultrasonic transducer according to one or more embodiments. Referring to FIG. 9, components of the ultrasonic transducer of the current embodiment may be the same as those of the ultrasonic transducer of the previous embodiment except for a side electrode substrate 131'. The side electrode substrate 131' may include a substrate body 1311' and a plurality of wiring lines 1312' provided on one surface 1311a' of the substrate body 1311'. The substrate body 1311' may be formed of an electric insulating material. In addition, the substrate body 1311' may be formed of a sound absorbing material such as a high molecular material, for example, an epoxy resin. The one surface 1311a' of the substrate body 1311' may be attached to the side surfaces of the piezoelectric elements 121 on which the side electrodes 125 may be provided. The substrate body 1311' of the current embodiment may have an insulating property, and thus the side electrode substrate 131' may be substantially the same as the side electrode substrates 131 described with reference to FIGS. 5 and 7 except for a location where the wiring lines 1312' may be formed. In other words, the wiring lines 1312' of the current embodiment may be formed in the one surface 1311a' where the substrate body 1311' may meet the piezoelectric elements 121. The wiring lines 1312' may include first parts 1312a' that may directly contact the side electrodes 125 of the piezoelectric elements 121, second parts 1312b' that may extend toward a first side end 1311c' of the substrate body 1311', and third parts 1312c' that may be exposed to the first side end 1311c' of the substrate body 1311'. Wiring patterns of the side electrode substrates 131' may vary according to the patterns of the side electrodes 125 of the piezoelectric elements 121.

Figure 10:
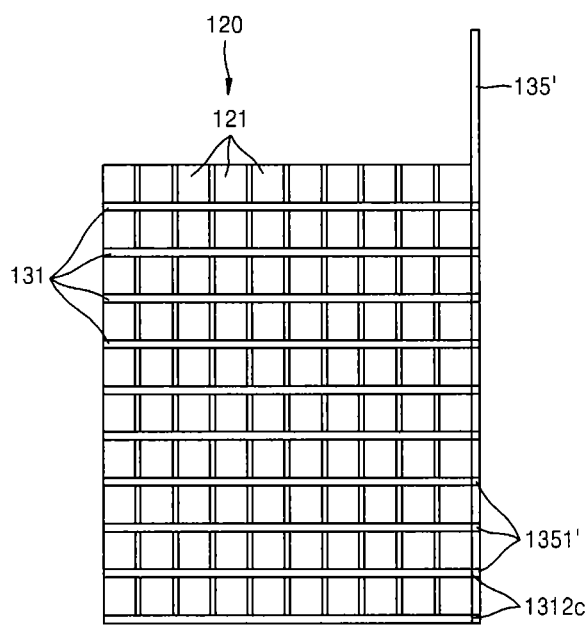
FIG. 10 is a view illustrating a side electrode substrate and a connection substrate bonded together in an ultrasonic transducer according to one or more embodiments.

FIG. 10 is a view illustrating a side electrode substrate and a connection substrate bonded together in an ultrasonic transducer according to one or more embodiments. Referring to FIG. 10, the third parts 1312c of the wiring lines 1312 exposed in the side electrode substrates 131 may be located in the same direction, and thus the current embodiment is different from the above-described embodiment in that only one connection substrate 135' is used in the current embodiment. For example, the side electrode substrates 131 may have the same wiring patterns as those of the first side electrode substrates 131a as described with reference to FIG. 5. Accordingly, all the third parts 1312c of the wiring lines 1312 of the side electrode substrates 131 may be located in the same direction. Also, in correspondence to the wiring patterns of the side electrode substrates 131, the piezoelectric elements 121 of all columns may have patterns in which the heights H of the side electrodes 125 are decreased in the column-wise direction (Y direction) similar to the piezoelectric elements 121a of the odd numbered columns described with reference to FIG. 5. The connection substrate 135' may include a plurality of connection terminals 1351' provided to contact the third parts 1312c of the side electrode substrates 131. Thus, the lower electrodes 124 of all the piezoelectric elements 121 may be electrically connected to the outside via the side electrodes 125 extending from the lower electrodes 124, the side electrode substrates 131, and the one connection substrate 135'.

In the above-described embodiments, the side electrode substrates 131 and 131' are formed in such a way that side ends of the side electrode substrates 131 and 131' may correspond to an outer side surface of an assembly of the piezoelectric elements 121 arranged in a rectangular shape, and thus the wiring lines 1312 and 1312' of the side electrode substrates 131 and 131' may be drawn to the outside by using the connection substrates 135, 136, and 135'. In other cases, the connection substrates 135, 136, and 135' may be omitted. For example, the one side ends of the side electrode substrates 131 and 131' may extend out of the outer side surface of the assembly of the piezoelectric elements 121 arranged in a rectangular shape to be directly connected to an outer cable.

Figure 11:
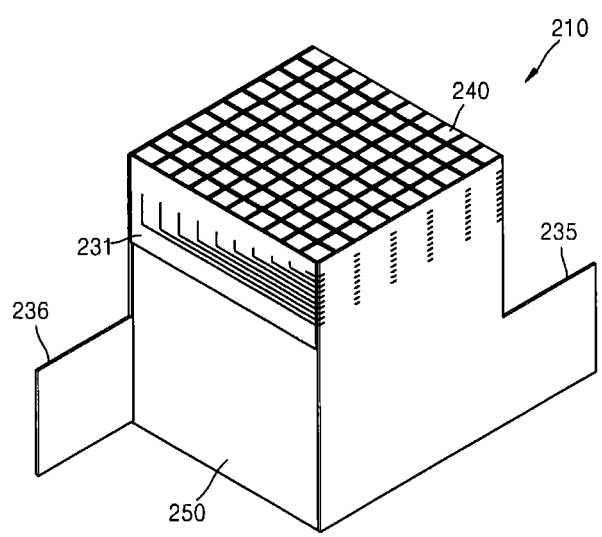
FIG. 11 is a perspective view of an ultrasonic transducer according to one or more embodiments.
Figure 12:
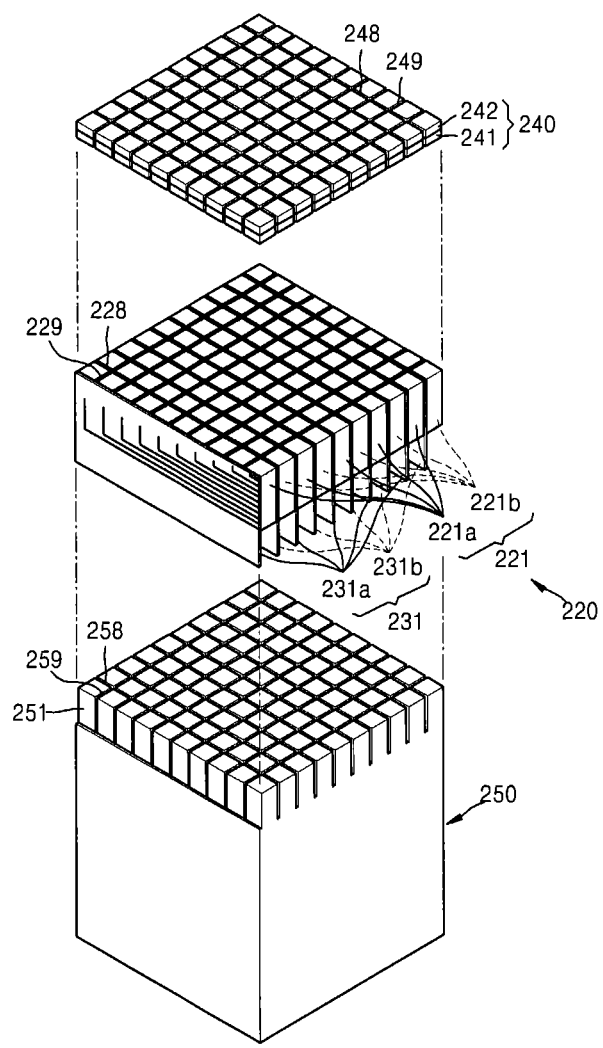
FIG. 12 is an exploded perspective view of an ultrasonic transducer according to one or more embodiments.

FIG. 11 is a perspective view of an ultrasonic transducer 210 according to one or more embodiments. FIG. 12 is an exploded perspective view of the ultrasonic transducer 210 according to one or more embodiments. For convenience of description, in FIG. 12, first and second connection substrates 235 and 236 are omitted. Also, although top ends of side electrode substrates 231 correspond to top surfaces of piezoelectric elements 221 in FIG. 12, the top ends of the side electrode substrates 231 may extend to correspond to top surfaces of acoustic matching layers 240.

Referring to FIGS. 11 and 12, the ultrasonic transducer 210 of one or more embodiments may include, for example a piezoelectric layer 220, an electrode connecting unit 230 for electrical connection of the piezoelectric layer 220, the acoustic matching layers 240 disposed on a top surface of the piezoelectric layer 220, and/or a rear surface supporting unit 250 disposed on a bottom surface of the piezoelectric layer 220.

The piezoelectric layer 220 may include a plurality of piezoelectric elements 221. The piezoelectric elements 221 may be arranged spaced apart from one another on a two-dimensional plane in lines and columns. The piezoelectric elements 221 may be distinguished in units of columns, and thus patterns of electrodes of piezoelectric elements 221a of odd numbered columns may be different from patterns of electrodes of piezoelectric elements 221b of even numbered columns.

The electrode connecting unit 230 may include the side electrode substrates 231 electrically connected to upper electrodes 223 (see FIG. 13) of the piezoelectric elements 221 and first and second connection substrates 235 and 236 that may be electrically connected to the side electrode substrates 231.

The side electrode substrates 231 may be attached to side surfaces of the piezoelectric elements 221. The patterns of the electrodes of the piezoelectric elements 221a of the odd numbered columns may be different from the patterns of the electrodes of the piezoelectric elements 221b of the even numbered columns, and thus wiring patterns of the odd-numbered side electrode substrates 231a may be different from those of the even-numbered side electrode substrates 231b.

The first and second connection substrates 235 and 236 may be substrates for integrating the wiring lines of the side electrode substrates 231 and may be attached to outer surfaces of the piezoelectric elements 221. The first connection substrate 235 may be electrically connected to the odd-numbered side electrode substrates 231a, and the second connection substrate 236 may be electrically connected to the even-numbered side electrode substrates 231b.

The acoustic matching layers 240 may be provided on the top surface of the piezoelectric layer 220. The acoustic matching layers 240 may be respectively provided on the top surfaces of the piezoelectric elements 221 to be spaced apart from one another. The acoustic matching layers 240 each may include two layers 241 and 242 having different acoustic impedances. In other cases, the acoustic matching layers 240 may consists of a single layer or three or more layers. An acoustic lens (not shown) for focusing an ultrasonic wave traveling forward on a specific point may further be provided on the acoustic matching layers 240.

The rear surface supporting unit 250 is a block for supporting the piezoelectric layer 220. An upper portion 251 of the rear surface supporting unit 250 may include a plurality of unit blocks spaced apart from one another to correspond to the piezoelectric elements 221. In other words, horizontal gaps 258 and vertical gaps 259 may be formed in the upper portion 251 of the rear surface supporting unit 250 to correspond to vertical gaps 259 and horizontal gaps 229 between the piezoelectric elements 221. The rear surface supporting unit 250 may be entirely formed of a conductive material, or at least the upper portion 251 of the rear surface supporting unit 250 may be formed of a conductive material. When the piezoelectric layer 220 is supported by the rear surface supporting unit 250, lower electrodes 224 (see FIG. 14) of the piezoelectric elements 221 may be electrically connected to the rear surface supporting unit 250, and thus the entire rear surface supporting unit 250 may serve as a common electrode or at least the upper portion 251 of the rear surface supporting unit 250 may serve as a common electrode. The lower electrodes 224 of the piezoelectric elements 221 may be omitted, and thus the rear surface supporting unit 250 may directly serve as a lower electrode.

Figure 13:
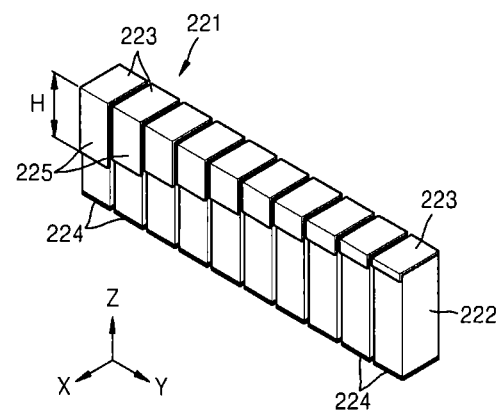
FIG. 13 is a view illustrating piezoelectric elements of an ultrasonic transducer according to one or more embodiments.

FIG. 13 is a view illustrating the piezoelectric elements 221 arranged in any one column from among the piezoelectric elements 221 arranged in lines and columns in the ultrasonic transducer 210 of FIG. 12. Referring to FIG. 13, the piezoelectric elements 221 may include piezoelectric bodies 222 and upper and lower electrodes 223 and 224 respectively provided on top and bottom surfaces of the piezoelectric bodies 222. The upper electrodes 223 may be individual electrodes respectively provided in the piezoelectric elements 221 and may be signal electrodes to which signals are independently applied. The lower electrodes 224 may be common electrodes of the piezoelectric elements 121. The upper electrodes 223 may extend to one side surfaces of the piezoelectric materials 222 to from side electrodes 225. The side electrodes 225 may be located on the side surfaces of the piezoelectric elements 221 arranged in a line in the same direction. Also, heights H of the side electrodes 225 may be formed to be different from one another. As shown in FIG. 13, the heights H of the side electrodes 225 may be formed to be gradually decreased or increased in the column-wise direction (Y direction). If necessary, the heights H of the side electrodes 225 may be formed to be equal to one another.

Figure 14:
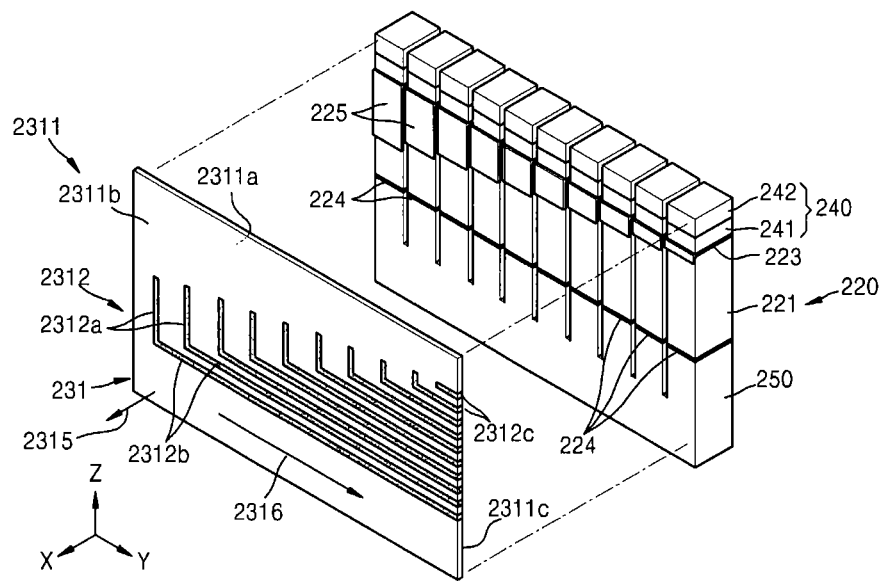
FIG. 14 is a view illustrating a side electrode substrate attached to side surfaces of piezoelectric elements according to one or more embodiments.

FIG. 14 is a view illustrating the side electrode substrates 231 attached to the side surfaces of piezoelectric elements 221 according to one or more embodiments. Referring to FIG. 14, the side electrode substrates 231 may be attached to the side surfaces of the piezoelectric elements 221 on which the side electrodes 225 are provided.

In one or more embodiments, the side electrode substrates 231 each may include a substrate body 2311 and wiring lines 2312 provided in the substrate body 2311. The substrate body 2311 may be formed of an anisotropic electroconductive material having an electroconductive property in a thickness direction 2315 and having an insulating property in a surface direction 2316. One surface 2311a of the substrate body 2311 may be attached to the side surfaces of the piezoelectric elements 221 on which the side electrodes 225 may be provided. The wiring lines 2312 may be provided in a surface 2311b opposite to the one surface 2311a of the substrate body 2311. The wiring lines 2312 may include first parts 2312a of which at least a part may overlap with the side electrodes 225 of the piezoelectric elements 121 by interposing the substrate body 2311 therebetween, second parts 2312b which may extend toward a first side end 2311c of the substrate body 2311, and third parts 2312c which may be exposed by the first side end 2311c of the substrate body 2311. Since the substrate body 2311 may have an electroconductive property in the thickness direction 2315, the side electrodes 225 of the piezoelectric elements 221 and the first parts 2312a may be electrically connected to each other. The substrate body 2311 may have an insulating property in the surface direction 2316, and thus an electric insulating property may be maintained between adjacent wiring lines 2312. Accordingly, the upper electrodes 223 of the piezoelectric elements 221 may be connected to the outside via the side electrode substrates 231. Meanwhile, the lower electrodes 224 of the piezoelectric elements 221 may be connected to the outside via the rear surface supporting unit 250 having a conductive property.

Patterns of the side electrodes 225 of the piezoelectric elements 221a of the odd numbered columns and wiring patterns of the odd-numbered side electrode substrates 231a, and patterns of the side electrodes 225 of the piezoelectric elements 221b of the even numbered columns and wiring patterns of the even-numbered side electrode substrates 231b may vary substantially in the same way as the example described with reference to FIG. 7. In other words, the piezoelectric elements 221a (see FIG. 12) of the odd numbered columns may be exposed by the third parts 2312c of the substrate body 2311 to be electrically connected to the first connection substrate 235, and the wiring lines 2312 of the piezoelectric elements 221b of the even numbered columns may be exposed to a side end opposite to the third parts 2312c of the substrate body 2311 to be electrically connected to the second connection substrate 236.

In the ultrasonic transducer 210 of one or more embodiments, the side electrodes 225 of the piezoelectric elements 121 may be formed to extend from the upper electrodes 223, and thus the ultrasonic transducer 210 may be substantially the same as the ultrasonic transducer 110 of one or more embodiments described with reference to FIGS. 1 to 8 except that the wiring patterns of the side electrode substrates 231 and locations of the common electrodes of the current embodiment may be changed from those of one or more previous described embodiments.

Figure 15:
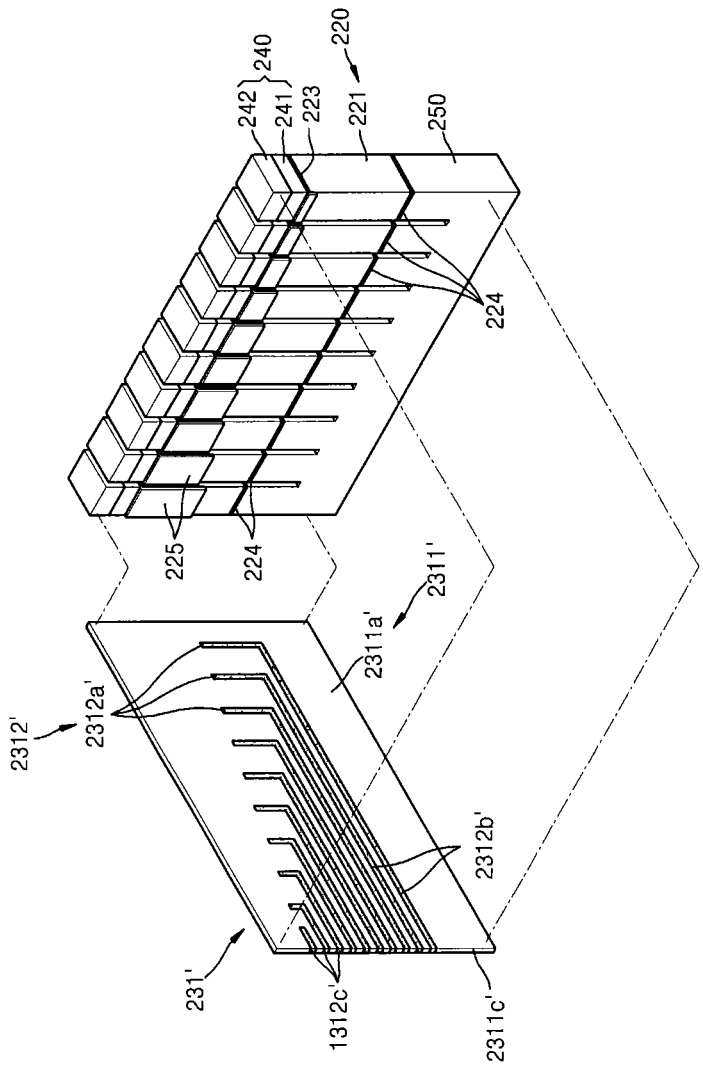
FIG. 15 is a view illustrating a side electrode substrate attached to side surfaces of piezoelectric elements in an ultrasonic transducer according to one or more embodiments.

FIG. 15 is a view illustrating a side electrode substrate attached to side surfaces of piezoelectric elements in an ultrasonic transducer according to one or more embodiments. Referring to FIG. 15, components of the ultrasonic transducer of the current embodiment may be the same as those of the ultrasonic transducer of one or more embodiments described with reference to FIGS. 11 to 14 except for a side electrode substrate 231'. The side electrode substrate 231' may include a substrate body 2311' and wiring lines 2312' provided on one surface 2311a' of the substrate body 2311'. The substrate body 2311' may be formed of an electric insulating material. The one surface 2311a' of the substrate body 2311' may be attached to the side surfaces of the piezoelectric elements 221 on which the side electrodes 225 may be provided. The substrate body 2311' of the current embodiment may be substantially the same as the side electrode substrates 231 described with respect to FIG. 14 except for the fact that locations where the wiring lines 2312' may be formed are different from those where the wiring lines 2312 may be formed. In other words, the wiring lines 2312' of one or more embodiments may be formed in the one surface 2311a' where the substrate body 2311' meets the piezoelectric elements 221. The wiring lines 2312' may include first parts 2312a' of which at least some directly contact the side electrodes 225 of the piezoelectric elements 221, second parts 2312b' which may extend toward a first side end 2311c' of the substrate body 2311', and third parts 1312c' which may be exposed by the first side end 2311c' of the substrate body 2311'. As described above with reference to FIG. 14, wiring patterns of the side electrode substrates 231' may vary according to the patterns of the side electrodes 225 of the piezoelectric elements 221.

Figure 16:
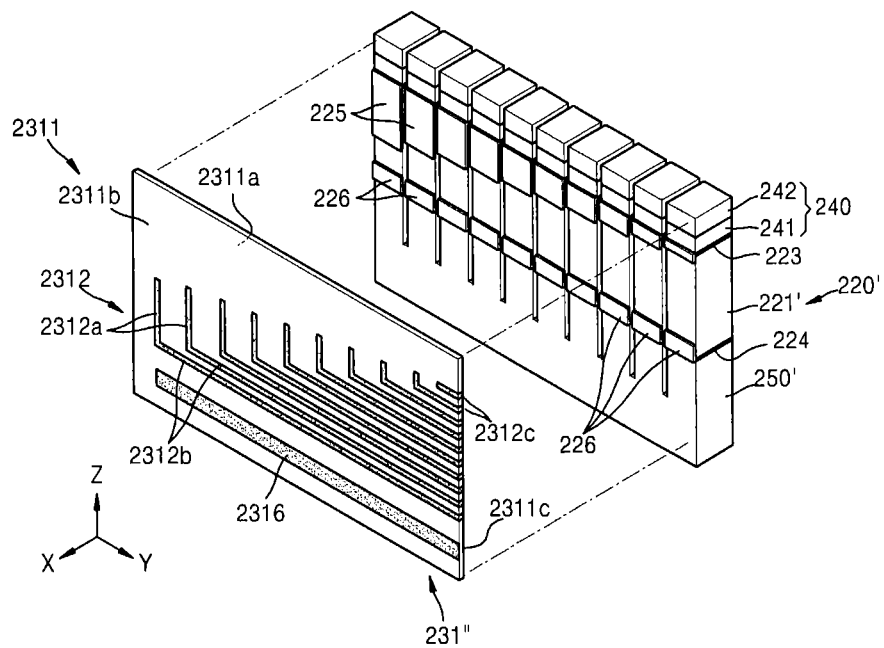
FIG. 16 is a view illustrating a side electrode substrate and a connection substrate bonded together in an ultrasonic transducer according to one or more embodiments.

FIG. 16 is a view illustrating a side electrode substrate and a connection substrate bonded together in an ultrasonic transducer according to one or more embodiments.

Referring to FIG. 16, components of the ultrasonic transducer of the current embodiment may be the same as those of the ultrasonic transducer of one or more embodiments described with reference to FIGS. 12 to 14 except for an electrical connection structure of the lower electrodes 224 of a plurality of piezoelectric elements 221'. In the current embodiment, the rear surface supporting unit 250 may be formed of an insulating material. Thus, the rear surface supporting unit 250 may not be used as a common electrode of the piezoelectric elements 221'. Accordingly, in the current embodiment, the lower electrodes 224 may be individually provided on bottom surfaces of the piezoelectric elements 221', and the lower electrodes 224 may extend toward side surfaces of the piezoelectric elements 221' to form lower side electrodes 226. Also, a second wiring line 2316 commonly corresponding to the lower side electrodes 226 of the piezoelectric elements 221' may be provided in the one surface 2311a of a side electrode substrate 231". In other words, the second wiring line 2316 may face the lower side electrodes 226 of the piezoelectric elements 221' by interposing the substrate body 2311 of the side electrode substrate 231" therebetween, and may be simultaneously and electrically connected to the lower side electrodes 226 by electric anisotropy of the substrate body 2311. An end of the second wiring line 2316 may be exposed by the first side end 2311c of the side electrode substrate 231" similar to the third parts 2312c of the wiring lines 2312. Accordingly, the lower electrodes 224 of the piezoelectric elements 221' may be electrically connected to the outside or grounded via the side electrode substrate 231" and the first and second connection substrates 235 and 236 (see FIG. 11).

Next, a method of manufacturing an ultrasonic transducer according to an embodiment of the present invention will be described.

FIGS. 17A to 17K illustrate a method of manufacturing an ultrasonic transducer according to one embodiment of the present invention.

Figure 17A:
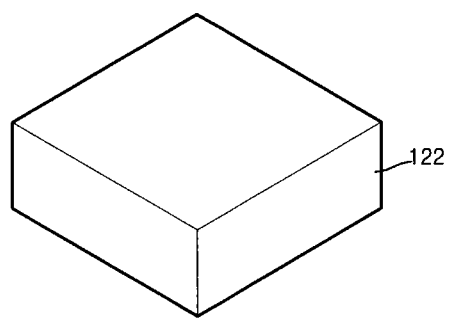
FIGS. 17A to 17K are views illustrating a method of manufacturing an ultrasonic transducer according to one or more embodiments.
Figure 17B:
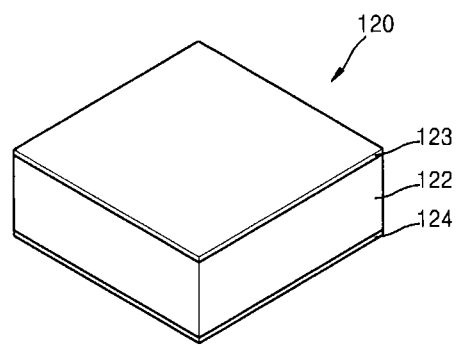

As shown in FIG. 17A, the piezoelectric bodies 122 having a flat plate shape may be prepared. As shown in FIG. 17B, the upper and lower electrodes 123 and 124 may be respectively provided on the top and bottom surfaces of the piezoelectric bodies 122 to form the piezoelectric layer 120.

Figure 17C:
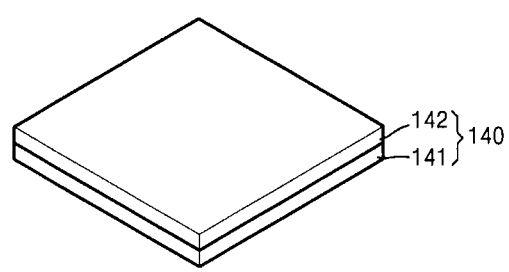
Figure 17D:
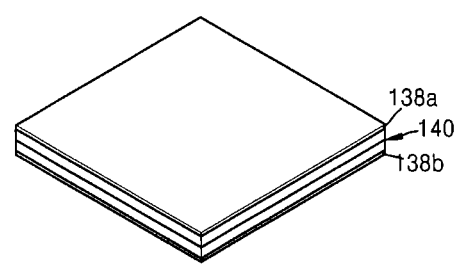

Similarly, as shown in FIG. 17C, the acoustic matching layers 140 having a flat plate shape may be prepared. The acoustic matching layers 140 may include the two layers 141 and 142 having different acoustic impedances. As shown in FIG. 17D, upper and lower electrodes 138a and 138b may be formed on the top surfaces and bottom surfaces of the acoustic matching layers 140. Any one of the upper electrode 123 of the piezoelectric layer 120 and the lower electrode 138b of the acoustic matching layers 140 may be omitted.

Figure 17E:
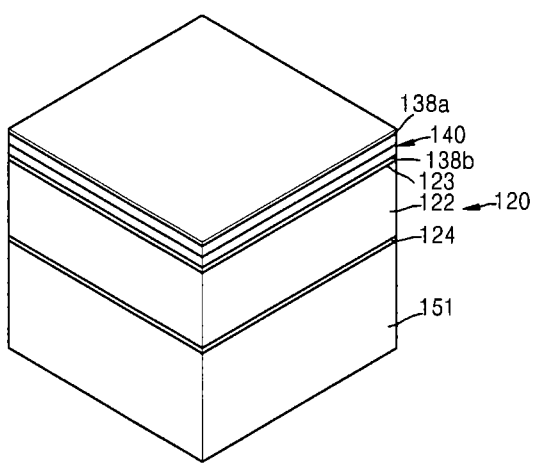

As shown in FIG. 17E, the piezoelectric layer 120 may be bonded to the support structure 151, and the acoustic matching layers 140 may be bonded to a top surface of the piezoelectric layer 120. The upper electrode 123 of the piezoelectric layer 120 and the lower electrode 138b of the acoustic matching layers 140 may be bonded together.

Figure 17F:
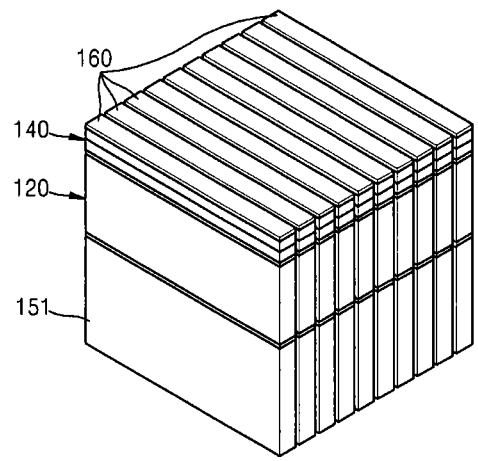
Figure 17G:
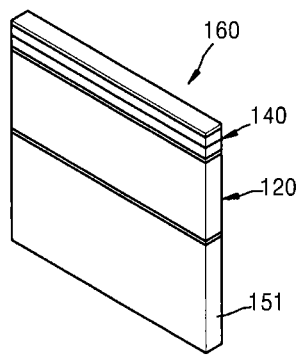

As shown in FIG. 17F, a block including the piezoelectric layer 120 and the acoustic matching layers 140 having flat plate shapes may be cut in a vertical direction at equal intervals to form a plurality of sub-blocks 160. FIG. 17G illustrates the divided single sub-block 160. The sub-block 160 may have a rectangular parallelepiped shape that is relatively long in one direction.

Figure 17H:
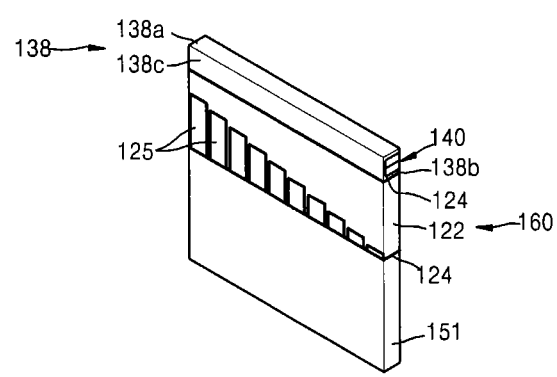

As shown in FIG. 17H, electrode patterns may be formed on a side surface of the sub-block 160. In other words, the side electrodes 125 electrically connected to the lower electrodes 124 of the piezoelectric bodies 122 may be formed on the side surfaces of the piezoelectric bodies 122, and a side electrode 138c for electrically connecting the upper electrode 138a and the lower electrode 138b formed on the top and bottom surfaces of the acoustic matching layers 140 may be formed on side surfaces of the acoustic matching layers 140. The upper electrode 138a, the lower electrode 138b, and the side electrode 138c formed in the acoustic matching layer 140 together may form the intermediate electrode layer 138. The heights of the side electrodes 125 formed on the side surfaces of the piezoelectric body 122 may be formed to be gradually decreased or increased in a lengthwise direction of the sub-block 160 as described above.

Figure 17I:
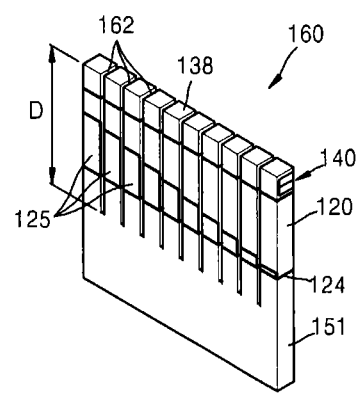

As shown in FIG. 17I, a plurality of kerfs 162 may be formed in the sub-block 160 in a depth direction at equal intervals. The kerfs 162 may be formed in such a way that heights of the kerfs 162 reach a predetermined position of the support structure 151. In the sub-block 160, the piezoelectric elements 121 may correspond to the piezoelectric elements 121 arranged in the column-wise direction in one or more embodiments described with reference to FIG. 4.

Figure 17J:
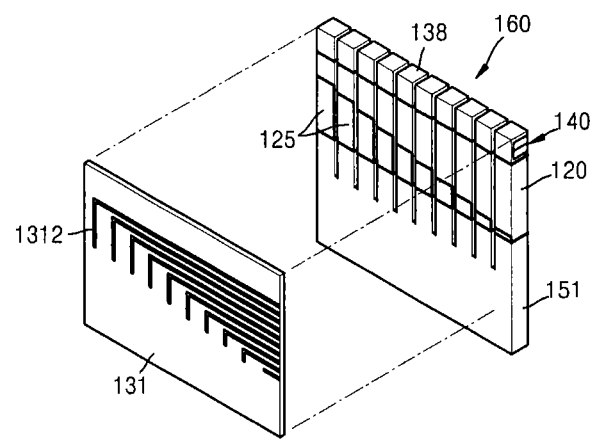

As shown in FIG. 17J, the side electrode substrates 131 in which the wiring lines 1312 are provided may be bonded to a surface of the sub-block 160 in which the side electrodes 125 may be formed.

Figure 17K:
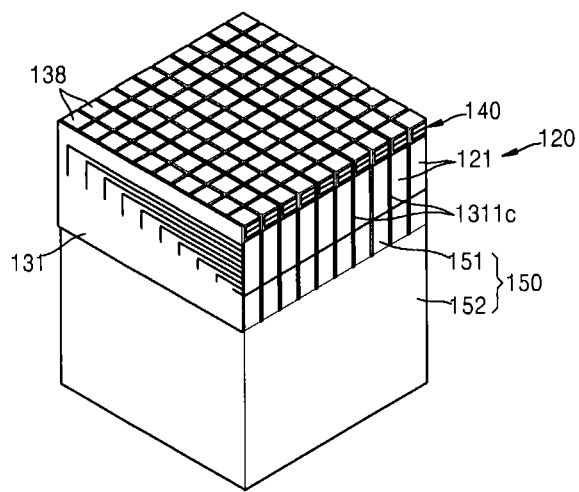

As shown in FIG. 17K, the sub-blocks 160 to which the side electrode substrates 131 may be bonded may be arranged to be tightly adhered to a top surface of a supporting block 152. The support structure 151 and the supporting block 152 may be formed of the same material or different materials. The common electrode plate 139 (see FIG. 2) may be bonded to the top surfaces of the acoustic matching layers 140, and the first and second connection substrates 135 and 136 (see FIG. 2) may be bonded to the side ends of the side electrode substrates 131, thereby completing the manufacture of the ultrasonic transducer 110 as shown in FIG. 2.

Before the sub-blocks 160 to which the side electrode substrates 131 are bonded are bonded to the supporting block 152, a process for detecting a piezoelectric property by applying voltages individually to the sub-blocks 160 may be additionally performed. In a conventional method of manufacturing an ultrasonic transducer, a piezoelectric layer is formed by using one piezoelectric material, but it is not easy to uniformly provide a piezoelectric characteristic over the entire piezoelectric material in terms of a characteristic of the piezoelectric material. As a result, in a conventional ultrasonic transducer, a piezoelectric characteristic may be not uniformly provided over an entire area of a plurality of piezoelectric elements arranged in a two-dimensional array. Meanwhile, according to the method of manufacturing an ultrasonic transducer of the present invention, when the single ultrasonic transducer 110 is manufactured, since the piezoelectric layer 120 is formed by coupling the sub-blocks 160 in units of columns, each sub-block 160 is tested before coupling the sub-blocks 160 and the sub-blocks 160 not having a uniform piezoelectric characteristic equal to or greater than a reference value are discarded, and thus dispersion of the piezoelectric characteristics of the piezoelectric elements 121 is decreased, thereby reducing a fluctuation in performance of the ultrasonic transducer 110 as much as possible.

FIGS. 18A to 18J illustrate a method of manufacturing an ultrasonic transducer according to another embodiment of the present invention.

Figure 18A:
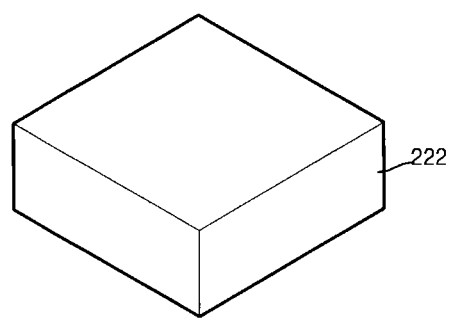
FIGS. 18A to 18J are views illustrating a method of manufacturing an ultrasonic transducer according to one or more embodiments.
Figure 18B:
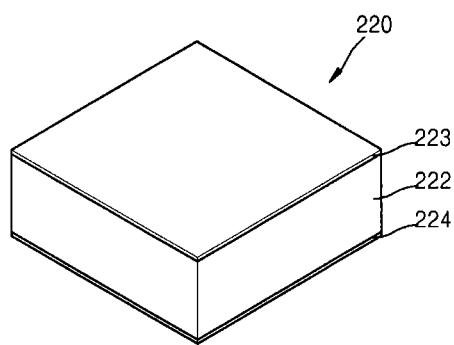

As shown in FIG. 18A, the piezoelectric bodies 222 having a flat plate shape may be prepared. As shown in FIG. 18B, the upper and lower electrodes 223 and 224 may be provided on the top and bottom surfaces of the piezoelectric bodies 222 to form the piezoelectric layer 220.

Figure 18C:
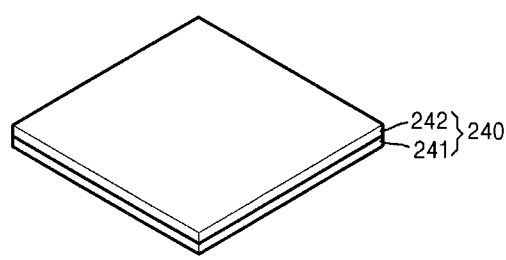

As shown in FIG. 18C, the acoustic matching layers 240 having a flat plate shape may be prepared. The acoustic matching layer 240 may include the two layers 241 and 242 having different acoustic impedances.

Figure 18D:
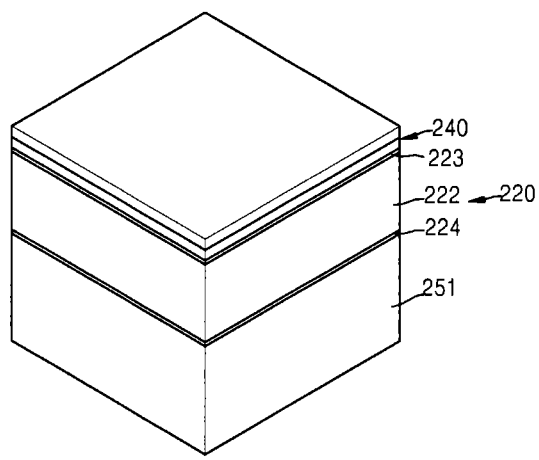

As shown in FIG. 18D, the piezoelectric layer 220 may be bonded to the support structure 251, and the acoustic matching layers 240 may be bonded to the top surface of the piezoelectric layer 220. The support structure 251 may be formed of a conductive material.

Figure 18E:
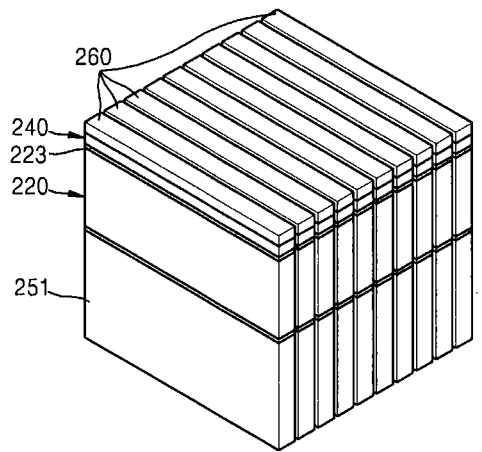
Figure 18F:
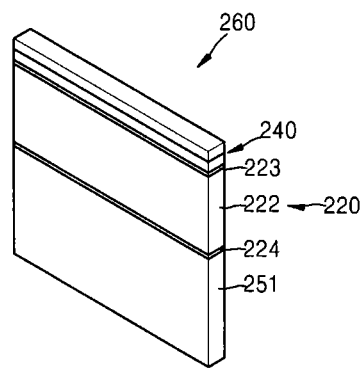

As shown in FIG. 18E, a block including the piezoelectric layer 220 and the acoustic matching layers 240 having flat plate shapes may be cut in a vertical direction at equal intervals. FIG. 18F illustrates one of a plurality of divided sub-blocks 260.

Figure 18G:
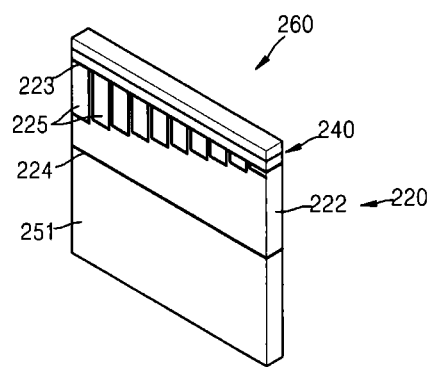

As shown in FIG. 18G, an electrode pattern may be formed in a side surface of the sub-block 260. In other words, the side electrodes 225 electrically connected to the upper electrode 223 of the piezoelectric bodies 222 may be formed in side surfaces of the piezoelectric bodies 222. The side electrodes 225 formed in the side surfaces of the piezoelectric material 222 may be formed in such a way that heights of the side electrodes 225 are gradually decreased or increased as described above.

Figure 18H:
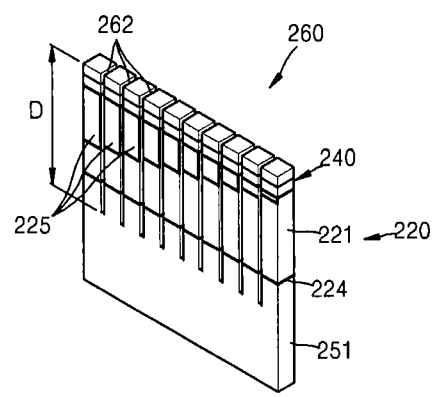

As shown in FIG. 18H, a plurality of kerfs 262 may be formed in the sub-block 260 in a depth direction at equal intervals. The kerfs 262 may be formed in such a way that heights of the kerfs 262 may reach a predetermined position of the support structure 251.

Figure 18I:
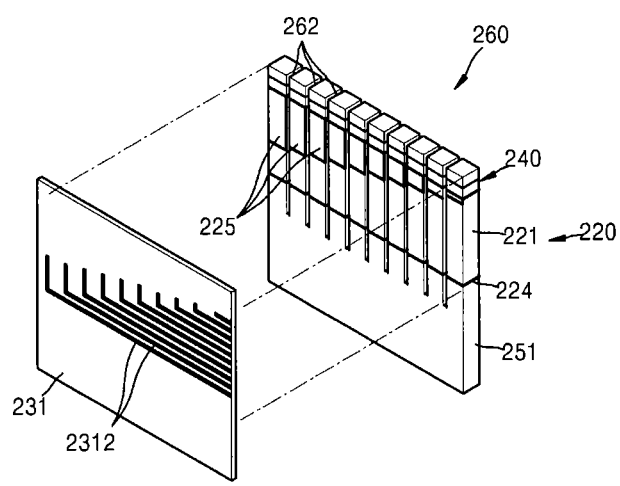

As shown in FIG. 18I, the side electrode substrates 231 in which the wiring lines 2312 may be provided may be bonded to a surface of the sub-block 260 in which the side electrodes 225 may be formed.

Figure 18J:
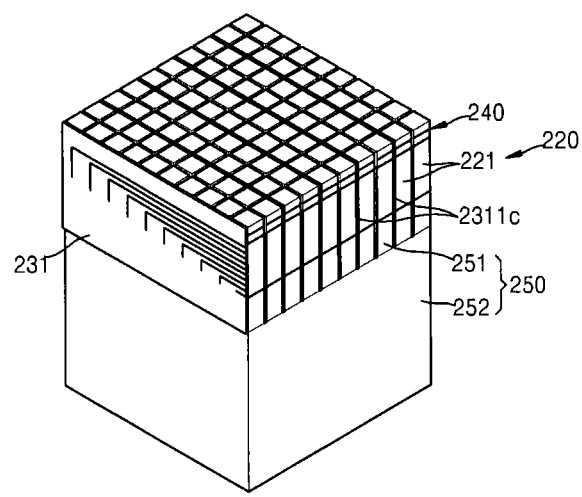

As shown in FIG. 18J, the sub-blocks 260 to which the side electrode substrates 231 may be bonded may be arranged to be fixed to a top surface of a supporting block 252. The support structure 251 and the supporting block 252 together may form the rear surface supporting unit 250. The support structure 251 and the supporting block 252 may be formed of the same material or different materials. The first and second connection substrates 235 and 236 (see FIG. 11) may be bonded to side ends of the side electrode substrate 231, thereby completing the manufacture of the ultrasonic transducer 210 as shown in FIG. 11.

The ultrasonic transducer, the ultrasonic probe, and the ultrasound image diagnosis apparatus according to the above-described one or more embodiments have the following effects.

Firstly, electrical signals may be respectively applied to a plurality of piezoelectric elements via a side electrode, and thus an electric connecting structure via the side electrode may be easily applied to a two-dimensional arrayed ultrasonic transducer, and further to a stacked structured ultrasonic transducer.

Secondly, when a single ultrasonic transducer is manufactured, a plurality of piezoelectric elements may be assembled in units of columns, and thus the piezoelectric elements may be tested in units of columns to decrease dispersion of piezoelectric characteristics, thereby possibly reducing a fluctuation in performance of the ultrasonic transducer.

While aspects of the present invention has been particularly shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if the described techniques are performed in a different order and/or if components in a described system, architecture, device, or circuit are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. An ultrasonic transducer comprising:
   a plurality of piezoelectric elements arranged in at least one column;
   individual electrodes provided on at least one surface of top and bottom surfaces of each of the plurality of piezoelectric elements;
   a plurality of side electrodes each extending from the individual electrodes along one side surface of a corresponding piezoelectric element among the plurality of piezoelectric elements; and
   a side electrode substrate comprising a plurality of wiring lines bonded to the one side surface of the corresponding piezoelectric element among the plurality of piezoelectric elements and electrically connected to the plurality of side electrodes, respectively,
   wherein the plurality of piezoelectric elements are arranged in a two-dimensional array to be spaced apart from one another in columns and lines, and a plurality of the side electrode substrates, including the side electrode substrate, are inserted into gaps between the columns of the plurality of piezoelectric elements, and
   wherein heights of the plurality of side electrodes of the piezoelectric elements of a first column are decreased in a lengthwise direction of the first column, and heights of the plurality of side electrodes of the piezoelectric elements of a second column adjacent to the first column are increased in the lengthwise direction of the second column.

2. The ultrasonic transducer of claim 1, wherein the plurality of wiring lines of the side electrode substrate comprise first parts respectively facing the plurality of side electrodes, second parts extending toward one side ends of the side electrode substrate, and third parts exposed by the one side ends of the side electrode substrate.

3. The ultrasonic transducer of claim 2, wherein a substrate body of the side electrode substrate is formed of an anisotropic electroconductive material having an electroconductive property in a thickness direction and having an insulating property in a surface direction, and the plurality of wiring lines of the side electrode substrate are provided in a surface opposite to a surface where the side electrode substrate meets the side electrodes of the piezoelectric elements.

4. The ultrasonic transducer of claim 2, wherein the substrate body of the side electrode substrate is formed of an electric insulating material, and the plurality of wiring lines of the side electrode substrate are provided in the surface where the substrate meets the side electrodes.

5. The ultrasonic transducer of claim 1, wherein the plurality of wiring lines of the plurality of side electrode substrates comprise first parts respectively facing the plurality of side electrodes, second parts extending toward side ends of the plurality of side electrode substrates, and third parts exposed by the side ends of the plurality of side electrode substrates, and the side ends by which the third parts are exposed of a first side electrode substrate bonded to the piezoelectric elements of the first column are opposite to the side ends by which the third parts are exposed of a second side electrode substrate bonded to the piezoelectric elements of the second column.

6. The ultrasonic transducer of claim 5, further comprising a first connection substrate electrically connected to the exposed third parts of the first side electrode substrate and a second connection substrate electrically connected to the exposed third parts of the second side electrode substrate.

7. The ultrasonic transducer of claim 1, wherein a substrate body of the side electrode substrate is formed of a sound absorbing material.

8. The ultrasonic transducer of claim 1, wherein a substrate body of the side electrode substrate is formed of a flexible material.

9. The ultrasonic transducer of claim 1, wherein the individual electrodes provided on the bottom surfaces of each of the piezoelectric elements comprise signal electrodes, and the individual electrodes provided on the top surfaces of each of the piezoelectric elements comprise common electrodes.

10. The ultrasonic transducer of claim 9, wherein the common electrodes further comprise upper electrode plates provided on top surfaces of each of the common electrodes, respectively, each of the upper electrode plates being commonly and electrically connected to each of the common electrodes, respectively.

11. The ultrasonic transducer of claim 10, further comprising an acoustic matching layer provided between the common electrodes and an upper electrode layer, the acoustic matching layer being formed of a conductive material or at least a portion of an outer surface of the acoustic matching layer being coated with a conductive material.

12. The ultrasonic transducer of claim 1, wherein the individual electrodes provided on the top surfaces of each of the piezoelectric elements comprise signal electrodes, and the individual electrodes provided on the bottom surfaces of each of the piezoelectric elements comprise common electrodes.

13. The ultrasonic transducer of claim 12, further comprising a rear surface supporting unit provided under the piezoelectric elements to support the piezoelectric elements, the rear surface supporting unit being formed of a conductive material and being electrically connected to the common electrodes.

14. The ultrasonic transducer of claim 1, further comprising an acoustic matching layer located above each of the piezoelectric elements.

15. The ultrasonic transducer of claim 1, further comprising a rear surface supporting unit provided under the piezoelectric elements to support the piezoelectric elements.

16. The ultrasonic transducer of claim 15, further comprising a plurality of kerfs formed in portions of the rear surface supporting unit to correspond to gaps between the piezoelectric elements.

17. The ultrasonic transducer of claim 15, wherein at least a portion of the rear surface supporting unit contacting the piezoelectric elements is formed of a sound absorbing material.

18. The ultrasonic transducer of claim 1, wherein a first part of each of the plurality of wiring lines of the side electrode substrate is in contact with and at least partially overlaps a portion of each side electrode.

19. An ultrasonic transducer comprising:
a plurality of piezoelectric elements arranged in at least one column;
individual electrodes provided on at least one surface of top and bottom surfaces of each of the plurality of piezoelectric elements;
a plurality of side electrodes each extending from the individual electrodes along one side surface of a corresponding piezoelectric element among the plurality of piezoelectric elements; and
a side electrode substrate comprising a plurality of wiring lines bonded to the one side surface of the corresponding piezoelectric element among the plurality of piezoelectric elements and electrically connected to the plurality of side electrodes, respectively,
wherein the plurality of piezoelectric elements are arranged in a two-dimensional array to be spaced apart from one another in columns and lines, and a plurality of the side electrode substrates, including the side electrode substrate, are inserted into gaps between the columns of the plurality of piezoelectric elements, and
wherein heights of the plurality of side electrodes of the plurality of piezoelectric elements of all columns are decreased or increased in the same direction.

20. The ultrasonic transducer of claim 19, wherein the plurality of wiring lines of the plurality of side electrode substrates comprise first parts respectively facing the plurality of side electrodes, second parts extending toward one side ends of the side electrode substrate, and third parts exposed by the one side ends of the side electrode substrate, wherein the side ends by which the third parts are exposed of the plurality of side electrode substrates are arranged in the same direction.

21. The ultrasonic transducer of claim 20, further comprising one connection substrate electrically connected to the exposed third parts of the plurality of side electrode substrates.

22. An ultrasonic probe comprising:
an ultrasonic transducer; and
a housing accommodating the ultrasonic transducer,
wherein the ultrasonic transducer comprises:
a plurality of piezoelectric elements arranged in at least one column;
individual electrodes provided on at least one surface of top and bottom surfaces of each of the plurality of piezoelectric elements;
a plurality of side electrodes each extending from the individual electrodes along one side surface of a corresponding piezoelectric element among the plurality of piezoelectric elements; and
a side electrode substrate comprising a plurality of wiring lines bonded to the one side surface of the plurality of piezoelectric elements and electrically connected to the plurality of side electrodes, respectively, wherein the plurality of piezoelectric elements are arranged in a two-dimensional array to be spaced apart from one another in columns and lines, and a plurality of the side electrode substrates, including the side electrode substrate, are inserted into gaps between the columns of the plurality of piezoelectric elements, and wherein heights of the plurality of side electrodes of the piezoelectric elements of a first column are decreased in a lengthwise direction of the first column, and heights of the plurality of side electrodes of the piezoelectric elements of a second column adjacent to the first column are increased in the lengthwise direction of the second column.

23. An ultrasound image diagnosis apparatus comprising:

an ultrasonic probe comprising an ultrasonic transducer and a housing accommodating the ultrasonic transducer; and a signal processor for generating an ultrasonic wave image based on an ultrasonic wave echo signal detected by the ultrasonic probe, wherein the ultrasonic transducer comprises:

a plurality of piezoelectric elements arranged in at least one column;

individual electrodes provided on at least one surface of top and bottom surfaces of each of the plurality of piezoelectric elements;

a plurality of side electrodes each extending from the individual electrodes along one side surface of a corresponding piezoelectric element among the plurality of piezoelectric elements; and a side electrode substrate comprising a plurality of wiring lines bonded to the one side surface of the plurality of piezoelectric elements and electrically connected to the plurality of side electrodes, respectively, wherein the plurality of piezoelectric elements are arranged in a two-dimensional array to be spaced apart from one another in columns and lines, and a plurality of the side electrode substrates, including the side electrode substrate, are inserted into gaps between the columns of the plurality of piezoelectric elements, and wherein heights of the plurality of side electrodes of the piezoelectric elements of a first column are gradually decreased in a lengthwise direction of the first column, and heights of the plurality of side electrodes of the piezoelectric elements of a second column adjacent to the first column are gradually increased in the lengthwise direction of the second column.

* * * * *